(12) United States Patent
Sorensen

(10) Patent No.: US 9,041,395 B2
(45) Date of Patent: May 26, 2015

(54) MRI METHOD OF CALCULATING AND GENERATING SPATIALLY-TAILORED PARALLEL RADIO FREQUENCY SATURATION FIELDS

(75) Inventor: Alma Gregory Sorensen, Belmont, MA (US)

(73) Assignee: The General Hospital Corporation, Boston, MA (US)

( * ) Notice: Subject to any disclaimer, the term of this patent is extended or adjusted under 35 U.S.C. 154(b) by 701 days.

(21) Appl. No.: 13/250,691

(22) Filed: Sep. 30, 2011

(65) Prior Publication Data

US 2012/0197103 A1    Aug. 2, 2012

Related U.S. Application Data

(60) Provisional application No. 61/388,150, filed on Sep. 30, 2010.

(51) Int. Cl.
| | | |
|---|---|---|
| A61B 5/05 | (2006.01) | |
| G01R 33/483 | (2006.01) | |
| G01R 33/565 | (2006.01) | |
| G01R 33/561 | (2006.01) | |

(52) U.S. Cl.
CPC ............ *G01R 33/4838* (2013.01); *A61B 5/05* (2013.01); *G01R 33/5612* (2013.01); *G01R 33/56509* (2013.01)

(58) Field of Classification Search
USPC .............. 324/300–322, 338; 600/407–435; 382/128–131; 315/3.5, 375
See application file for complete search history.

(56) References Cited

U.S. PATENT DOCUMENTS

| 2,863,086 | A | * | 12/1958 | Cook | 315/3.5 |
|---|---|---|---|---|---|
| 2,900,562 | A | * | 8/1959 | Burns, Jr. | 315/375 |
| 3,286,163 | A | * | 11/1966 | Holser et al. | 324/338 |
| 4,761,613 | A | * | 8/1988 | Hinks | 324/309 |
| 7,627,359 | B2 | * | 12/2009 | Yarnykh et al. | 600/410 |
| 8,664,953 | B2 | * | 3/2014 | Morita | 324/309 |
| 8,680,860 | B2 | * | 3/2014 | Xu et al. | 324/309 |
| 2006/0184002 | A1 | * | 8/2006 | Yarnykh et al. | 600/410 |
| 2010/0201360 | A1 | * | 8/2010 | Morita | 324/309 |
| 2012/0146638 | A1 | * | 6/2012 | Xu et al. | 324/309 |
| 2012/0197103 | A1 | * | 8/2012 | Sorensen | 600/410 |
| 2013/0221961 | A1 | * | 8/2013 | Liu | 324/307 |

* cited by examiner

*Primary Examiner* — Melissa Koval
*Assistant Examiner* — Tiffany Fetzner
(74) *Attorney, Agent, or Firm* — Quarles & Brady, LLP

(57) ABSTRACT

A method for producing magnetic resonance images of a subject in which artifacts resulting from a localized source, such as from pulsatile blood flow, are substantially mitigated is provided. The location of an artifact source, at which spins corresponding to flowing blood are located, is identified. Using this identified artifact source location, a region-of-saturation is calculated. A magnetic resonance imaging (MRI) system is then directed to perform a pulse sequence that results in the generation of a radio frequency (RF) saturation field being produced by an array of RF transmission coils. The RF saturation field is sized and shaped according to the calculated region-of-saturation. Images are reconstructed from image data acquired after application of the RF saturation field, and artifacts related to motion of the spins at the identified location of the artifact source are substantially mitigated in these images.

13 Claims, 4 Drawing Sheets

MRI METHOD OF CALCULATING AND GENERATING SPATIALLY-TAILORED PARALLEL RADIO FREQUENCY SATURATION FIELDS

CROSS-REFERENCE TO RELATED APPLICATIONS

This application claims the benefit of U.S. Provisional Patent Application Ser. No. 61/388,150 filed on Sep. 30, 2010, and entitled "Methods, Systems, Apparatuses and Computer-Readable Media for Imaging."

BACKGROUND OF THE INVENTION

The field of the invention is systems and methods for magnetic resonance imaging ("MRI"). More particularly, the invention relates to systems and methods for magnetic resonance angiography ("MRA") using a parallel transmission radio frequency ("RF") system.

A key challenge in MRI is the presence of pulsation or other artifacts, which degrade image quality. Typically, a part of the body such as a blood vessel in one location pulsates and causes streaking or other imaging artifacts in other parts of the image that are remote from the blood vessel. While there are methods, such as flow compensation, that can reduce such artifacts, such methods are often encumbered with tradeoffs that are undesirable in many circumstances. For example, flow compensation techniques lengthen the echo time unfavorably, thereby changing the image contrast.

It would therefore be desirable to provide a method for magnetic resonance imaging that was able to produce images of a subject in which flow-related image artifacts are substantially mitigated without requiring unfavorable flow-compensation techniques.

SUMMARY OF THE INVENTION

The present invention overcomes the aforementioned drawbacks by providing a method for calculating and generating a spatially-tailored parallel radio frequency saturation field that, when applied to an identified artifact source, results in the substantial mitigations of flow-related artifacts originating from spins at that location.

It is an aspect of the invention to provide a method for mitigating image artifacts resulting from blood flow using a magnetic resonance imaging ("MRI") system. A location of an artifact source at which spins corresponding to flowing blood are located is identified. For example, this artifact source location may be identified from an initially acquired image of the subject, such as an image acquired using phase contrast imaging. Identification of the artifact source location may also include an identification of the size and shape of artifact source. A region-of-saturation is calculated using the identified location of the artifact source. By way of example, the size and shape of the region-of-saturation may be calculated, and the shape of the region-of-saturation may be circular or, more generally, may be arbitrary. The MRI system is then directed to perform a pulse sequence that includes generating and applying a radio frequency ("RF") saturation field to the artifact source location. The RF saturation field is generated in accordance with the calculated region-of-saturation, and is generated by exciting a plurality of RF transmission coils that form an array of such coils. By way of example, RF transmission parameters are established using the calculated region-of-saturation and are provided as inputs to the array of RF transmission coils, such that the coils produce an RF saturation field that is sized and shaped in accordance with the calculated region-of-saturation. Image data is acquired following the application of the RF saturation field, from which images of the subject are reconstructed. Image artifacts related to motion of the spins at the identified location of the artifact source are substantially mitigated in these reconstructed images. An iterative optimization of the region-of-saturation may be performed, in which the efficacy of the artifact suppression is assessed in the reconstructed images and the region-of-saturation is recalculated accordingly, if desired.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

A method for localizing the source of a pulsation-related image artifact and using parallel transmission radio frequency ("RF") to target a region-of-saturation specific to the location of the artifact source is provided. The location of the artifact source is detected, for example, as a location corresponding to a high motion signal that is detected using a rapid phase contrast pulse sequence. The region-of-saturation is calculated from the identified artifact source location, and the size, shape, and location of the region-of-interest may be iteratively updated to result in better mitigation of the pulsation-related image artifacts. In addition, a plurality of regions-of-saturation may be utilized as a set of such regions-of-saturation. For example, a set of regions-of-saturation may be implemented to minimize the total amount of tissue that needs saturation. The shape of the region-of-saturation may be arbitrary. Using the provided method, parallel transmission hardware capabilities can be combined with an appropriate data acquisition to automate and optimize the placement of arbitrarily-shaped saturation bands and, thus, markedly improve image quality.

It is possible that potential sources of artifacts that cause image degradation other than a pulsation-related artifact can be present. These additional artifact sources can be detected with other methods besides phase change on phase contrast acquisition techniques. For example, the presence of fat can cause image artifacts on certain acquisitions, such as echo-planar imaging ("EPI") scans. For these situations, a pre-scan can be acquired to identify the source of the problem. Artifacts from the identified additional artifact sources can then be mitigated, for example, by the calculation and implementation of appropriate saturation bands placed to reduce or eliminate the fat signals.

Figure 1:
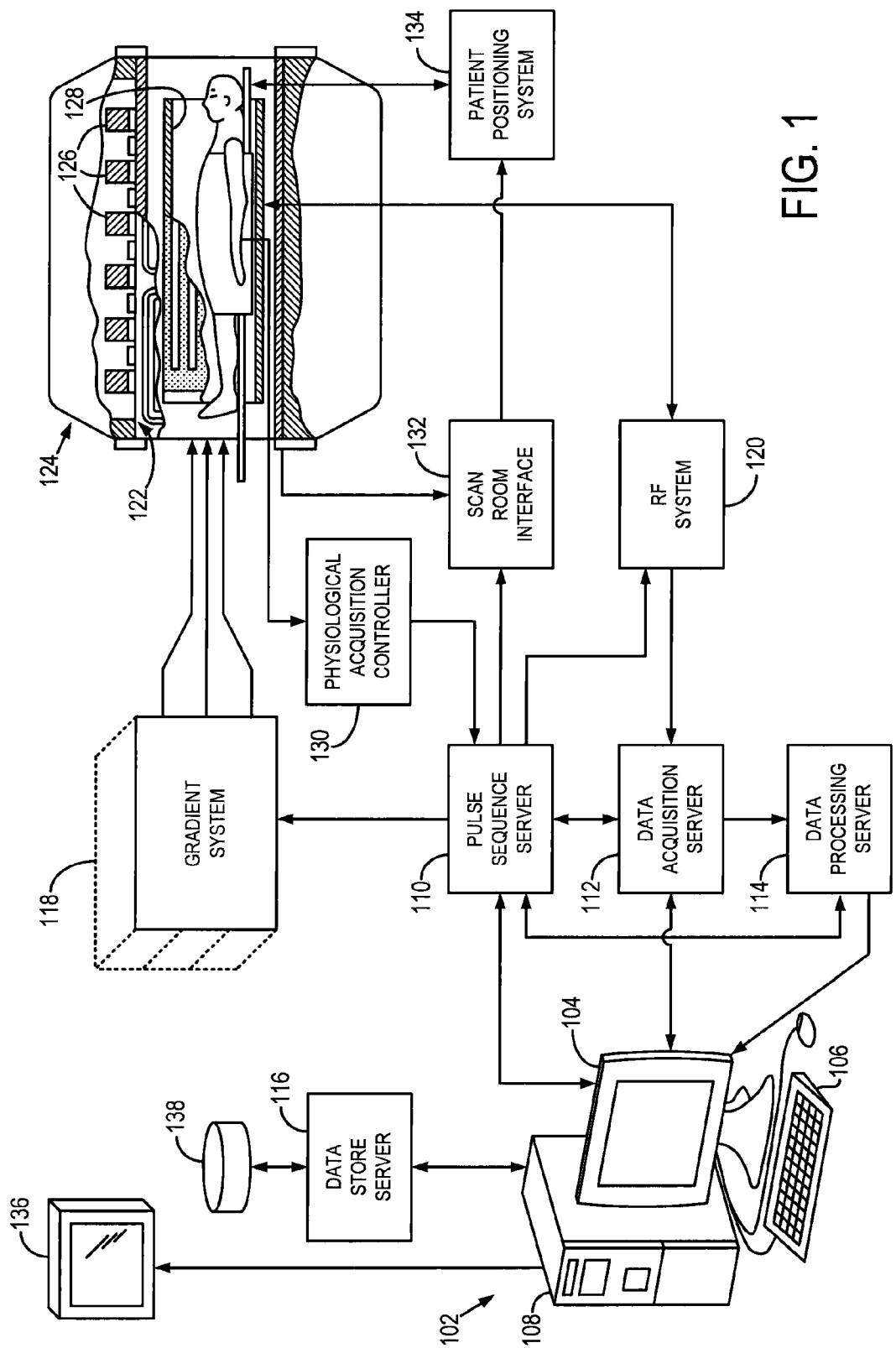
FIG. 1 is a block diagram of an example of a magnetic resonance imaging ("MRI") system.

Referring particularly now to FIG. 1, an example of a magnetic resonance imaging ("MRI") system 100 is illustrated. The MRI system 100 includes a workstation 102 having a display 104 and a keyboard 106. The workstation 102 includes a processor 108, such as a commercially available programmable machine running a commercially available operating system. The workstation 102 provides the operator interface that enables scan prescriptions to be entered into the MRI system 100. The workstation 102 is coupled to four servers: a pulse sequence server 110; a data acquisition server 112; a data processing server 114; and a data store server 116. The workstation 102 and each server 110, 112, 114, and 116 are connected to communicate with each other.

The pulse sequence server 110 functions in response to instructions downloaded from the workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding MR signals. The gradient coil assembly 122 forms part of a magnet assembly 124 that includes a polarizing magnet 126 and a whole-body RF coil 128.

RF excitation waveforms are applied to the RF coil 128, or a separate local coil (not shown in FIG. 1), by the RF system 120 to perform the prescribed magnetic resonance pulse sequence. Responsive MR signals detected by the RF coil 128, or a separate local coil (not shown in FIG. 1), are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays (not shown in FIG. 1).

The RF system 120 also includes one or more RF receiver channels. Each RF receiver channel includes an RF amplifier that amplifies the MR signal received by the coil 128 to which it is connected, and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2} \tag{1};$$

and the phase of the received MR signal may also be determined:

$$\phi = \tan^{-1}\left(\frac{Q}{I}\right). \tag{2}$$

The pulse sequence server 110 also optionally receives patient data from a physiological acquisition controller 130. The controller 130 receives signals from a number of different sensors connected to the patient, such as electrocardiograph ("ECG") signals from electrodes, or respiratory signals from a bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110. Also, navigator signals may be acquired during a scan and used to adjust the operating parameters of the RF system 120 or the gradient system 118, or to control the view order in which k-space is sampled. The data acquisition server 112 may also be employed to process MR signals used to detect the arrival of contrast agent in a magnetic resonance angiography ("MRA") scan. In all these examples, the data acquisition server 112 acquires MR data and processes it in real-time to produce information that is used to control the scan.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 114 are conveyed back to the workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network to other facilities.

Figure 2:
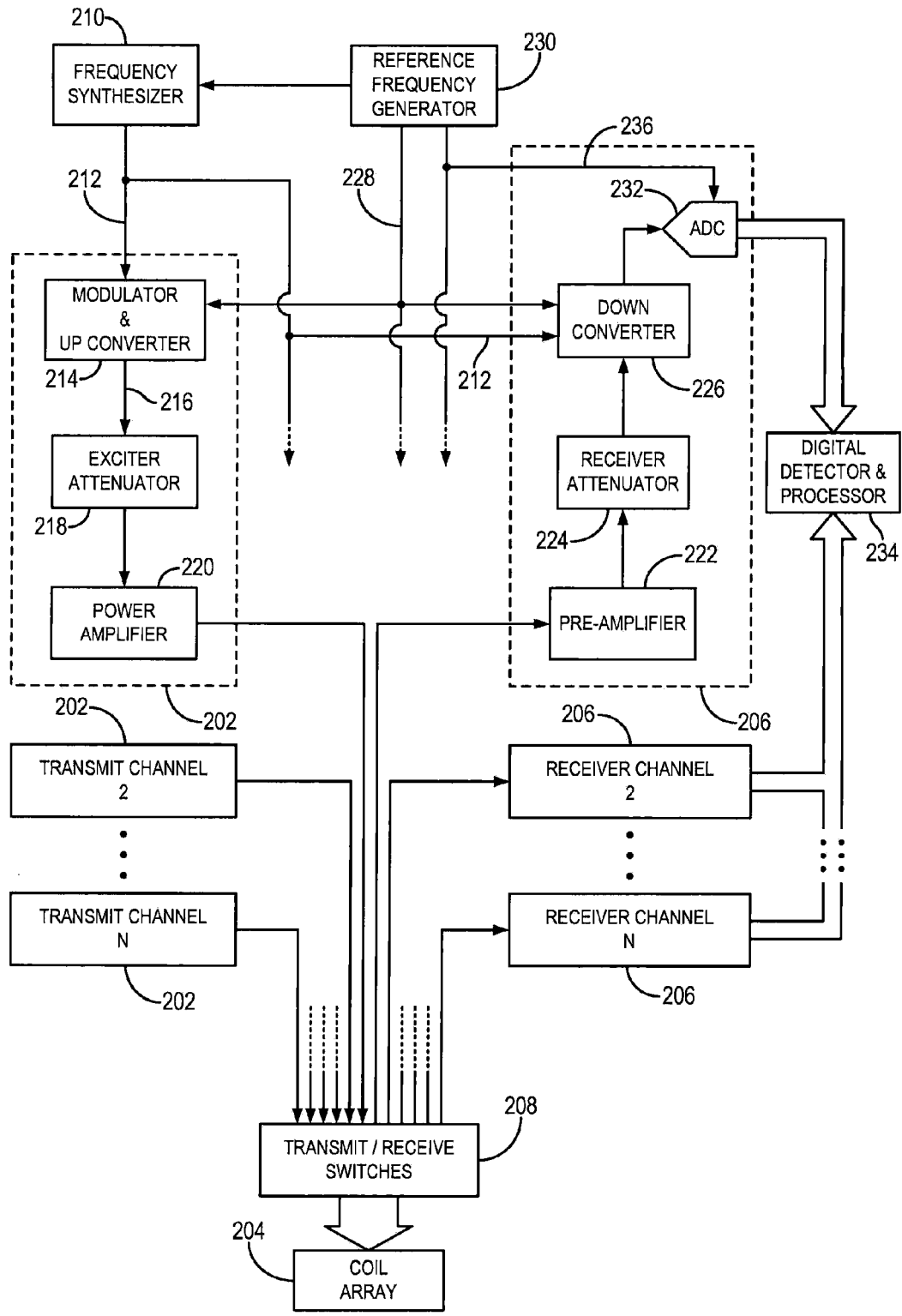
FIG. 2 is a block diagram of a radio frequency ("RF") system that forms part of the MRI system of FIG. 1.

As shown in FIG. 1, the radio frequency ("RF") system 120 may be connected to the whole body RF coil 128, or, as shown in FIG. 2, a transmission section of the RF system 120 may connect to one or more transmit channels 202 of an RF coil array 204 and a receiver section of the RF system 120 may connect to one or more receiver channels 206 of the RF coil array 204. The transmit channels 202 and the receiver channels 206 are connected to the RF coil array 204 by way of one or more transmit/receive ("T/R") switches 208.

Referring particularly to FIG. 2, the RF system 120 includes one or more transmit channels 202 that produce a prescribed RF excitation field. The base, or carrier, frequency of this RF excitation field is produced under control of a frequency synthesizer 210 that receives a set of digital signals from the pulse sequence server 110. These digital signals indicate the frequency and phase of the RF carrier signal produced at an output 212. The RF carrier is applied to a modulator and up converter 214 where its amplitude is modulated in response to a signal, R(t), also received from the pulse sequence server 110. The signal, R(t), defines the envelope of the RF excitation pulse to be produced and is produced by sequentially reading out a series of stored digital values. These stored digital values may be changed to enable any desired RF pulse envelope to be produced.

The magnitude of the RF excitation pulse produced at output 216 is attenuated by an exciter attenuator circuit 218 that receives a digital command from the pulse sequence server 110. The attenuated RF excitation pulses are then applied to a power amplifier 220 that drives the RF coil array 204.

The MR signal produced by the subject is picked up by the RF coil array 202 and applied to the inputs of the set of receiver channels 206. A preamplifier 222 in each receiver channel 206 amplifies the signal, which is then attenuated by a receiver attenuator 224 by an amount determined by a digital attenuation signal received from the pulse sequence server 110. The received signal is at or around the Larmor frequency, and this high frequency signal is down converted in a two step process by a down converter 226. The down converter 226 first mixes the MR signal with the carrier signal on line 212 and then mixes the resulting difference signal with a reference signal on line 228 that is produced by a reference frequency generator 230. The down converted MR signal is applied to the input of an analog-to-digital ("A/D") converter 232 that samples and digitizes the analog signal. The sampled and digitized signal is then applied to a digital detector and signal processor 234 that produces 16-bit in-phase (I) values and 16-bit quadrature (Q) values corresponding to the received signal. The resulting stream of digitized I and Q values of the received signal are output to the data acquisition server 112. In addition to generating the reference signal on line 228, the reference frequency generator 230 also generates a sampling signal on line 236 that is applied to the A/D converter 232.

Figure 3:
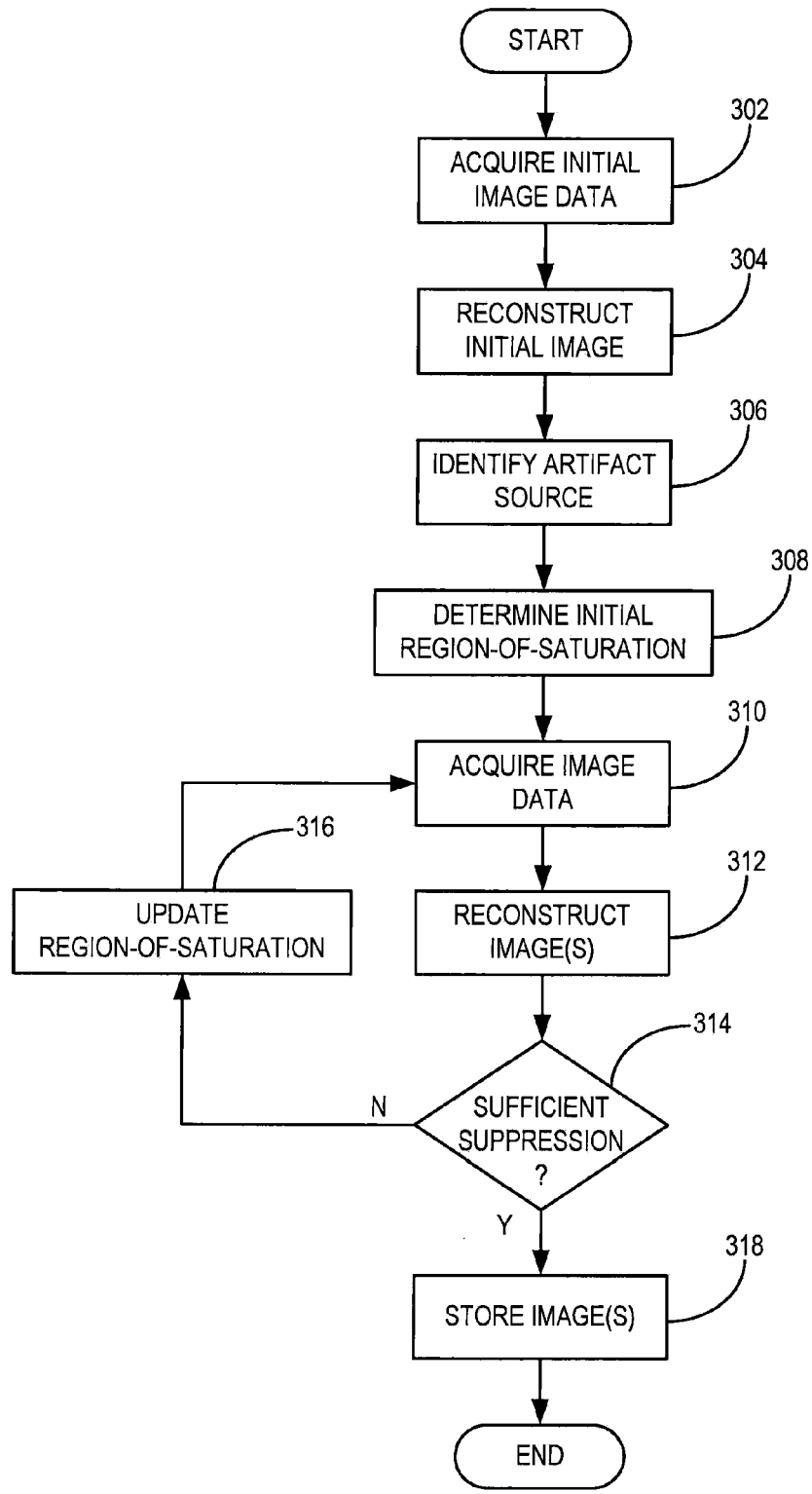
FIG. 3 is a flowchart setting forth the steps of an example of a method for saturating unwanted signals from a pulsation artifact source, thereby mitigating image artifacts resultant from pulsatile blood flow occurring at the artifact source.

Referring now to FIG. 3, a flowchart setting forth the steps of an example of a method for saturating unwanted signals from a pulsation artifact source, thereby mitigating image artifacts resultant from pulsatile blood flow occurring at the artifact source, is illustrated. It is noted that this method may be rapidly performed as part of a pre-scan, updated with motion correction during the acquisition of the scan, and so forth. The method begins with the acquisition of initial image data, as indicated at step 302. By way of example, the initial image data may be acquired with a phase contrast imaging technique such that blood vessels may be depicted in the resultant images. This initial data acquisition is preferably a rapid data acquisition that will be used primarily for identification of pulsation artifact sources. From the acquired initial image data, an initial image is reconstructed, as indicated at step 304. The initial image depicts the subject's anatomy in addition to potential sources of artifacts, such as regions containing pulsatile blood flow that may generate pulsation artifacts within or outside of a volume-of-interest. Using the reconstructed initial image, such sources of artifacts are identified, as indicated at step 306. Included in the identification of the location of such sources of artifacts is an identification of the size of such sources of artifacts.

Once the pulsation artifact source is identified, including its size and location, a calculation is performed to determine the initial region-of-saturation that may be used to mitigate the pulsation artifact, as indicated at step 308. Because this region-of-interest may be circular or rounded in shape, the region-of-saturation may also be referred to as a "saturation ball." However, it is noted that the region-of-saturation may be arbitrarily shaped. The region-of-saturation may be positioned over the identified artifact source so as to mitigate the generation of pulsation image artifacts.

Using the calculated or computed region-of-saturation, image data is now acquired, as indicated at step 310. By way of example, the image data is acquired with a phase contrast imaging technique, whereby radio frequency ("RF") saturation is provided to the region-of-saturation to mitigate unwanted image artifacts that would otherwise result from pulsatile blood flow occurring at the identified artifact source location. The region-of-saturation is communicated to an array of parallel transmission RF coils, which can be energized in a manner that produces an electromagnetic field that is sized, positioned, and shaped in accordance with the calculated region-of-saturation. As a result, the array of parallel transmission RF coils produce an RF saturation field substantially confined to the calculated region-of-saturation, thereby saturating substantially only those flowing spins at the artifact source that would otherwise generate the offending pulsation-related image artifact.

From this acquired image data, one or more images of the subject are reconstructed, as indicated at step 312. A determination may be made at decision block 314 whether the artifacts have been sufficiently mitigated in the reconstructed images. If not, the calculation of the region-of-saturation may be repeated to update the size, location, or both, of the region-of-saturation, as indicated at step 316. For example, the size of the region-of-saturation may be reduced so that it is more effective at suppressing only signals originating from the artifact source. Such iterative adjustment of the size and location of the region-of-saturation may be done to optimize the suppression of the signals origination from the artifact source. If it is determined at decision block 314 that the artifacts are sufficiently mitigated, then the reconstructed images are stored for review by a clinician, as indicated at step 318.

Figure 4A:
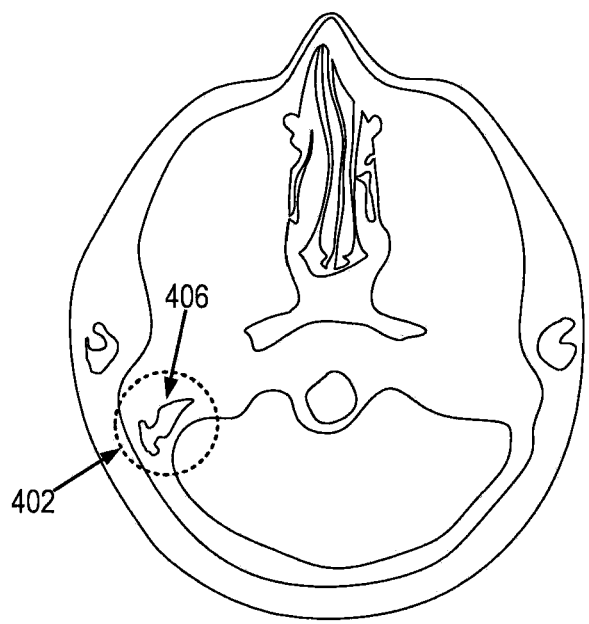
FIG. 4A is a graphic illustration of an example of a region-of-saturation calculated in accordance with the method of FIG. 3.
Figure 4B:
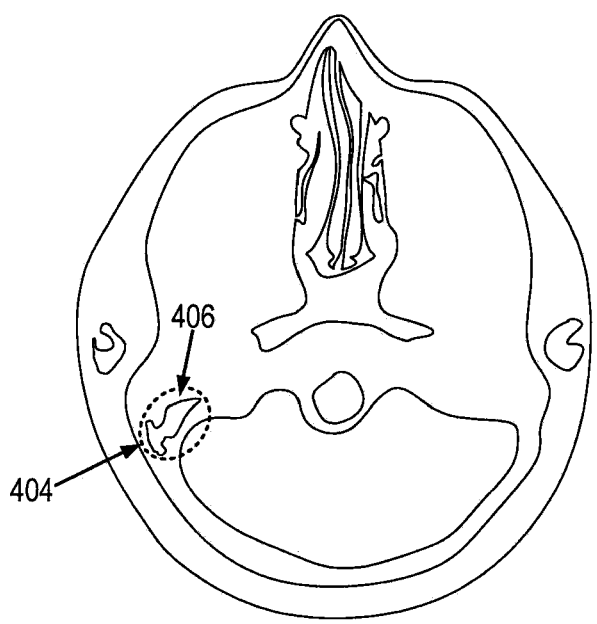
FIG. 4B is a graphic illustration of an example of an updated region-of-saturation calculated in accordance with the method of FIG. 3.

Referring now to FIGS. 4A and 4B, examples of an initial region-of-saturation 402 and an updated region-of-saturation 404 are illustrated. In FIG. 4A, an artifact source 406 has been identified as corresponding to a transverse venous sinus from an initial image. Accordingly, an initial region-of-saturation 402 is calculated and positioned over the artifact source 406. By way of example, it is determined that this initial region-of-saturation 402 does not provide sufficient mitigation of the pulsation-related image artifacts; thus, the size and shape of the region-of-saturation is refined and updated through an iterative process. The updated region-of-saturation 406 is illustrated in FIG. 4B. While above description provides an example using a 2D image, the same concepts can be applied to a 3D volume or even a 4D time series. In these cases, only during one part of the cardiac cycle does a saturation ball need to be applied and only to one part of the 3D volume acquisition.

The present invention contemplates various methods, systems, and apparatuses for achieving the imaging goals described and otherwise provided for herein. It is further contemplated that the present invention includes computer-readable storage media that is useful for carrying out one or more steps of the present methods and that may be used in conjunction with the present systems and apparatuses. By way of example, any hardware platform suitable for performing the processing described herein is suitable for use with the technology. Non-transitory computer-readable storage media refer to any medium or media that participate in providing instructions to a central processing unit ("CPU"), a processor, a microcontroller, or the like. Such media can take forms including, but not limited to, non-volatile and volatile media such as optical or magnetic disks and dynamic memory, respectively. Examples of non-transitory computer-readable storage media include a floppy disk; a hard disk; magnetic tape; any other magnetic storage medium; a CD-ROM disk; digital video disk ("DVD"); any other optical storage medium; random access memory ("RAM"), including static RAM ("SRAM") and dynamic RAM ("DRMA"); read only memory ("ROM"), including programmable ROM ("PROM"), erasable PROM ("EPROM"), and an electrically erasable PROM ("EEPROM"); and any other memory chip or cartridge.

The present invention has been described in terms of one or more preferred embodiments, and it should be appreciated that many equivalents, alternatives, variations, and modifications, aside from those expressly stated, are possible and within the scope of the invention.

The invention claimed is:

1. A method of mitigating an image artifact resulting from an artifact source using a magnetic resonance imaging (MRI) system, the steps of the method comprising:
    a) providing an initial magnetic resonance (MR) image acquired with an MRI system;
    b) identifying in the provided initial MR image, a location of an artifact source at which spins corresponding to the artifact source are located;
    c) calculating, based on the initial MR image data, a region-of-saturation using the identified location of the artifact source;
    d) directing the MRI system to perform a magnetic resonance pulse sequence that includes:
        i) applying at the location of the artifact source with an array of radio frequency (RF) transmission coils, an RF saturation field that is sized and shaped according to the calculated region-of-saturation;
        ii) acquiring MR image data following application of the RF saturation field; and
    e) reconstructing from the acquired MR image data, a reconstructed MRI image in which MR image artifacts related to a motion of the spins at the identified location of the artifact source are mitigated from the performance of steps d)i) and d)ii).

2. The method as recited in claim 1 in which step a) includes:
    i) Actively acquiring with the MRI system, initial image data;
    ii) reconstructing an initial image from the actively acquired initial image data.

3. The method as recited in claim 2 in which step a)i) includes acquiring the initial MR image data using a phase contrast pulse sequence.

4. The method as recited in claim 3 in which step b) includes identifying the location of the artifact source based on phase information in the initial MR image reconstructed in step a)ii).

5. The method as recited in claim 1 further comprising:
    f) evaluating the reconstructed MR image in order to assess a degree to which MR image artifacts related to a motion of the spins, as the identified location of the artifact source are mitigated;
    g) repeating step c) in order to calculate an updated region-of-saturation;
    h) repeating step d) using the updated region-of-saturation in order to acquire updated MR image data; and
    i) reconstructing an updated MR image from the acquired updated image data, in which MR image artifacts related to a motion of the spins at the identified location of the artifact source are mitigated to a larger degree in the updated MR image than in the MR image reconstructed in step e).

6. The method as recited in claim 1 in which step c) also includes calculating a size and a shape of the region-of-saturation.

7. The method as recited in claim 1 in which step b) also includes identifying a size and shape of the artifact source.

8. The method as recited in claim 1 in which step d)ii) also includes acquiring image data using a phase contrast pulse sequence.

9. The method as recited in claim 1 in which the artifact source is at least one of: flowing blood and a medical implant.

10. A non-transitory computer readable storage medium having stored thereon a computer program comprising instructions that when executed by a processor causes the processor to:
    a) receive a magnetic resonance image acquired with a magnetic resonance imaging (MRI) system;
    b) identify in the received magnetic resonance image, a location of the artifact source at which spins, corresponding to one of: an artifact and a potential artifact, in the magnetic resonance image, are located;
    c) calculate a region-of-saturation using the identified location of the artifact source;
    d) determine radio frequency (RF) transmission parameters that define inputs to an array of RF transmission coils, using the calculated region-of-saturation;
    e) communicate the determined RF transmission parameters as an input into an MRI system;
    f) direct the MRI system in order to perform a pulse sequence that includes operating the array of RF transmission coils in accordance with the communicated RF transmission parameters, such that an RF saturation field is produced by the array of RF transmission coils that saturates spins that are located at the identified location of the artifact source, after which magnetic resonance image data is acquired by the MRI system; and
    g) reconstruct a magnetic resonance image from the acquired magnetic resonance image data, wherein magnetic resonance image artifacts related to a motion of the spins at the identified location of the artifact source. Have been mitigated in the reconstructed magnetic resonance image by the RF saturation field produced by the array of RF transmission coils.

11. The non-transitory computer readable storage medium as recited in claim 10 in which step c) also includes calculating a size and shape of the region-of-saturation.

12. The non-transitory computer readable storage medium as recited in claim 11 in which the RF transmission parameters define inputs that when communicated as input into the array of RF transmission coils, cause the RF transmission coils in the array of RF transmission coils to produce an RF saturation field that is sized and shaped in accordance with the calculated size and shape of the region-of-saturation.

13. The non-transitory computer readable storage medium as recited in claim 10 in which steps c) and d) are each performed iteratively until an optimal region-of-saturation is determined.

* * * * *